(12) United States Patent
Taraboukhine (10) Patent No.: US 7,746,473 B2
(45) Date of Patent: *Jun. 29, 2010

(54) FULL SPECTRUM ADAPTIVE FILTERING (FSAF) FOR LOW OPEN AREA ENDPOINT DETECTION

(75) Inventor: Mikhail Taraboukhine, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 437 days.

This patent is subject to a terminal disclaimer.

(21) Appl. No.: 11/753,563

(22) Filed: May 24, 2007

(65) Prior Publication Data

US 2008/0291428 A1 Nov. 27, 2008

(51) Int. Cl.
*G01B 9/08* (2006.01)
(52) U.S. Cl. ........................................ 356/392
(58) Field of Classification Search ................ 356/392, 356/300

See application file for complete search history.

(56) References Cited

U.S. PATENT DOCUMENTS

| | | | |
|---|---|---|---|
| 4,415,402 A | 11/1983 | Gelernt et al. | |
| 4,936,937 A | 6/1990 | Burns et al. | |
| 5,362,356 A | 11/1994 | Schoenborn | |
| 5,910,011 A | 6/1999 | Cruse | |
| 6,263,255 B1 | 7/2001 | Tan et al. | |
| 6,455,437 B1 | 9/2002 | Davidow et al. | |
| 6,535,779 B1 | 3/2003 | Birang et al. | |
| 6,559,942 B2 | 5/2003 | Sui et al. | |
| 6,766,506 B1 | 7/2004 | Ratzlaff et al. | |
| 7,006,205 B2 | 2/2006 | Agarwal et al. | |
| 7,269,464 B2 | 9/2007 | Phillips et al. | |
| 2003/0163298 A1 | 8/2003 | Odom et al. | |
| 2004/0015940 A1 | 1/2004 | Heisey et al. | |
| 2005/0228523 A1 | 10/2005 | Heminway et al. | |
| 2006/0294372 A1 | 12/2006 | Maxa et al. | |
| 2007/0202613 A1* | 8/2007 | Usui et al. .................... 438/14 |
| 2009/0158265 A1* | 6/2009 | Davis et al. ................. 717/168 |

OTHER PUBLICATIONS

PCT International Search Report and Written Opinion dated Apr. 27, 2009 for International Appl. No. PCT/US2008/085900.

* cited by examiner

*Primary Examiner*—Roy Punnoose
(74) *Attorney, Agent, or Firm*—Patterson & Sheridan, LLP (57) ABSTRACT

A method for precise endpoint detection during etch processing of a substrate based on adaptive filtering of the optical emission spectrum (OES) data, even in low open area etching, is provided. Endpoint detection performed in this manner offers the benefits of increased signal-to-noise ratio and decreased computation costs and delay when compared to conventional endpoint detection techniques.

9 Claims, 6 Drawing Sheets

FULL SPECTRUM ADAPTIVE FILTERING (FSAF) FOR LOW OPEN AREA ENDPOINT DETECTION

BACKGROUND

1. Field

Embodiments of the present invention generally relate to substrate processing and, more particularly, to endpoint detection during etching of a substrate.

2. Description of the Related Art

A critical process in the fabrication of integrated circuits (ICs) is the removal of portions of various layers of materials formed on a substrate, such as a silicon wafer. Two of the most prevalent removal techniques are: 1) wet, or chemical etching, wherein a photoresist-patterned substrate is immersed in a chemical solution and 2) dry, or plasma etching, wherein a substrate is exposed to a bombardment of ions (e.g., a plasma of nitrogen, chlorine, and boron trichloride).

Plasma etching processes and apparatus are generally well-known for etching materials in semiconductor device fabrication. The process may begin with application of a masking material, such as photoresist, to a silicon wafer or other substrate. The masking pattern protects areas of the wafer from the etch process. The wafer may then be placed in a plasma reactor ("etcher") etched after a plasma is ignited. This process is especially valuable for the definition of small geometries.

Irrespective of the particular etch process being employed, it is generally of universal concern to detect when an overlying material ("film") has been completely removed ("cleared"). This is generally accomplished by detecting the presence of the underlying material, now exposed, in the plasma, such as by using an optical emissions spectroscopy (OES) technique.

With this technique, the OES equipment couples to a transparent window of a reaction chamber containing the plasma and monitors the optical emissions from the plasma. Conventionally, a single wavelength is extracted (filtered) from all of the emissions of the plasma, and the magnitude of the signal at the extracted wavelength indicates the present chemistry within the chamber. A change in this chemistry will increase or decrease the magnitude of the signal at the extracted wavelength and, as such, indicate a change in the process occurring within the chamber. For example, a plasma in a dry etch process is typically monitored by extracting the carbon monoxide (CO) emission line at 4835 Å. A change in the magnitude of the CO emission line is indicative of the endpoint of an oxide etch process.

Extracting a particular line, as well as suppressing the noise generated by the plasma at other wavelengths, requires substantial signal processing and careful OES equipment fabrication and calibration. Such endpoint detection requires the detection of a very small change in signal strength at a particular optical wavelength. As such, the desired signal is easily corrupted by noise. If care is not taken while monitoring the process, the endpoint may not be detected, and the wafer will be over etched. Such over etching may destroy the ICs on the wafer and reduce the yield of the semiconductor wafer processing system.

It is even more difficult to accurately monitor the etching process when the substrate being etched has a small open area between the etch-resistant features because the process signal from such a region is small relative to the process signal from other portions of the substrate. As used herein, the open area may be expressed as a percentage of the etch area to the surface area of the substrate. Conventional techniques that monitor the intensity of a particular emission wavelength are often limited to an open area of around 30% or larger. Smaller geometries in semiconductor processing may entail smaller etch open areas, even down to 1%, so conventional techniques may be inadequate.

Moreover, one type of signal processing technique used to detect etch endpoint involves neural principle component analysis (NPCA) known to those skilled in the art. However, NPCA requires lots of data and a corresponding amount of computation for endpoint detection, especially since the filter orders may be on the order of 20 to 100. Although processors are ever-increasing in speed, performing an NPCA may introduce significant delay between the actual occurrence of an event and the detection of that event, as much as a few seconds. During substrate processing where etching needs to be stopped immediately after the endpoint has occurred, such delay is unacceptable. Furthermore, the amount of computation required by NPCA monopolizes a substantial portion of the processor's power.

Accordingly, what is needed are techniques for a substrate processing system to precisely detect etch endpoint, especially for low open areas, without significant delay and with a lowered computation cost when compared to conventional endpoint detection techniques.

SUMMARY

Embodiments of the present invention generally relate to techniques for quick, precise etch endpoint detection during substrate processing. Techniques described herein may be suitable for embedded applications.

One embodiment of the invention is a method of detecting a desired etch state while etching a substrate. The method generally includes (a) providing first and second reference spectrums; (b) detecting optical emissions during etching of the substrate to generate a runtime optical emission spectrum (OES); (c) comparing the runtime OES with the first and second reference spectrums using adaptive filtering to generate a comparator output; and (d) repeating (b) and (c) until the desired etch state is detected based on the comparator output.

Another embodiment of the invention provides a computer-readable medium containing a program for detecting a desired etch state while etching a substrate. When executed by a processor, the program performs operations generally including (a) providing first and second reference spectrums; (b) detecting optical emissions during etching of the substrate to generate a runtime OES; (c) comparing the runtime OES with the first and second reference spectrums using adaptive filtering to generate a comparator output; and (d) repeating (b) and (c) until the desired etch state is detected based on the comparator output.

Yet another embodiment of the invention provides a digital filter for detecting a desired etch state while etching a substrate. The digital filter generally includes a runtime input; a first reference input; a second reference input; a first adaptive filter coupled to the runtime input and the first reference input and having a first filter output; a second adaptive filter coupled to the runtime input and the second reference input and having a second filter output; a third adaptive filter coupled to a compressed version of the first filter output and a compressed version of the second filter output and having a third filter output; and a fourth adaptive filter coupled to the third filter output and having a fourth filter output used as the output of the digital filter for desired etch state detection.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Embodiments of the present invention provide techniques for precise endpoint detection during etch processing of a substrate based on adaptive filtering of the optical emission spectrum (OES) data, even in low open area etching. Endpoint detection performed in this manner offers the benefits of increased signal-to-noise ratio and decreased computation costs and delay when compared to conventional endpoint detection techniques.

An Exemplary Substrate Etch System

Figure 1:
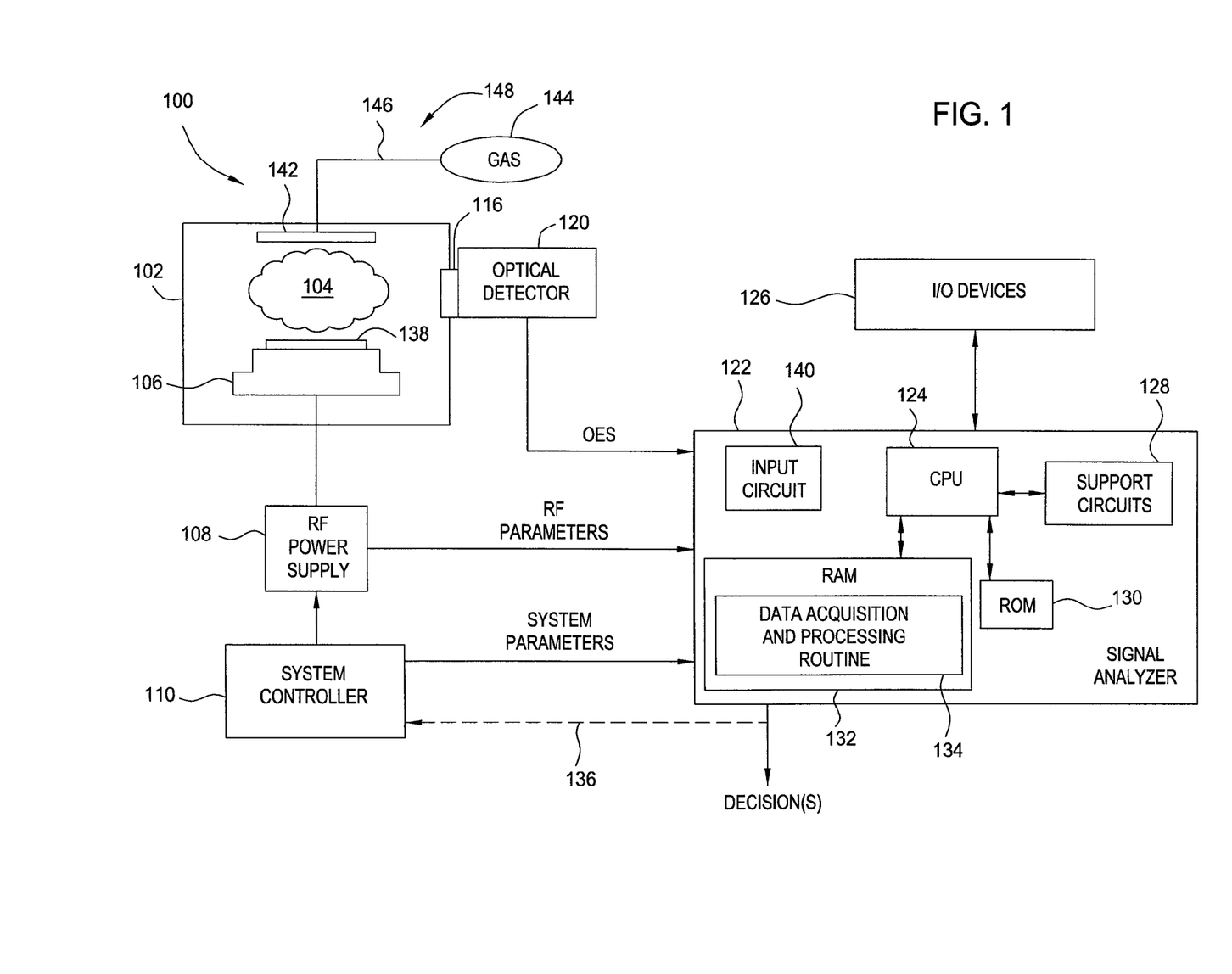
FIG. 1 is a block diagram of one embodiment of an exemplary substrate processing system for at least plasma etching the substrate.

FIG. 1 is a simplified functional block diagram of a semiconductor substrate processing system 100 coupled to a signal analyzer 122. The semiconductor substrate processing system 100 may comprise a reaction chamber 102 having a substrate support pedestal or susceptor 106, a radio frequency (RF) power supply 108, a reactive gas supply assembly 148, and a system controller 110. The pedestal 106 may support a substrate or semiconductor wafer 138 in the reaction chamber 102. The pedestal 106 may also form a cathode for the plasma generation system, and in such cases, the cathode may be coupled to the RF power supply 108. For example, in a plasma etching system a plasma may be generated by coupling RF power to a reactive gas. The reactive gas supply assembly 148 may be composed of a gas supply 144 that supplies a reactive gas via conduit 146 and manifold 142 to the reaction chamber 102. To ignite the plasma for some embodiments, RF power may be applied to the cathode. The chamber walls may be grounded, and the electric field between the chamber walls and the cathode may ignite a plasma 104 within the reaction chamber 102.

The system controller 110 may control the plasma-enhanced dry etching of the surface of the substrate 138 including, among other things, the RF power levels. This simplistic drawing of a semiconductor substrate processing system 100 is intended to be illustrative of the major components of the system. For a detailed description of an etch system, the reader should review U.S. Pat. No. 4,842,683 entitled "Magnetic Field-Enhanced Plasma Etch Reactor," issued Jun. 27, 1989.

The signal analyzer 122 may acquire data from a number of sources within the semiconductor substrate processing system 100. For example, optical emissions of the plasma 104 may be sensed through a transparent window 116 by an optical detector 120. The optical detector 120, shown in FIG. 1 positioned outside the chamber 102 directly in front of the window 116, may convert the optical energy that is coupled through the window 116 into an electrical signal, such as a voltage. The electrical signal may be transmitted as one parameter (e.g., an optical emission spectroscopy (OES) parameter) to the signal analyzer. The optical detector 120 may be any suitable multiple-wavelength optical detector device, such as a Fabry-Perot interferometer or an integrated charge-coupled device (CCD)-based spectrometer with a digital output. One suitable example is the SD1024D Series spectrograph available from Verity Instruments, which responds to wavelengths in the 200-800 nm range.

As described above, the system controller 110 may provide control signals to the RF power supply 108. In addition, the controller 110 may generate system parameter signals which are coupled to an input circuit 140 of the signal analyzer 122. The chamber 102 may also include a number of environmental sensors (not shown) such as temperature sensors, foreline and chamber pressure sensors, reactive gas analyzing sensors and the like. These sensors generally produce analog voltages that may also be coupled to the input circuit 140. The input circuit may synchronize, digitize, and buffer the data, as needed.

The signal analyzer 122 may be a general purpose computer having a central processing unit (CPU) 124, a plurality of input/output (I/O) devices 126, support circuits 128 (e.g., power supplies, clock circuits, bus controllers, cache, and the like), read-only memory (ROM) 130, and random access memory (RAM) 132. The interrelation and operation of these components of a general purpose computer are well known in the art.

The signal analyzer 122 may correlate all or a subset of the parameters that are provided as input to the analyzer. The data acquisition and processing routine 134 may be an executable software program which generally resides in RAM 132 as it is executed by the CPU 124. Decisions made in response to processing the parameters, such as stop etching based on etch endpoint detection, may be provided as an output of the signal analyzer 122. These decisions may be transmitted along path 136 to the system controller 110 for implementation. As such, the system controller 110 may react to these decisions by ending processing should endpoint detection have occurred or initiating a cleaning function if cleaning of the chamber is deemed required. The parameters and correlated data may also be stored in the RAM 132 for historical review of processing trends. Accordingly, new parameters may be determined for future monitoring.

Although the signal analyzer 122 is described herein as being a standalone general purpose computer that is programmed to perform the data acquisition and processing functions, these functions may be incorporated into the system controller 110 and executed on the microprocessor of the system controller for some embodiments. For other embodiments, the signal analyzer 122 may be part of an embedded controller or may be combined with the optical detector 120 in a spectrometer, for example, or other embedded application.

An Exemplary Adaptive Filter

To facilitate understanding of the techniques presented herein, it may be beneficial to introduce adaptive filters that may be employed in these techniques. As used herein, an adaptive filter generally refers to a filter which self-adjusts its transfer function according to an optimizing algorithm. Although analog versions may be envisioned, adaptive filters are typically digital filters because of the complexity of optimizing algorithms, performing digital signal processing and adjusting their performance based on the input signal. In other words, adaptive filters have dynamic filter coefficients that continually alter the transfer function.

In general, the adapting process involves the use of a cost function to feed an algorithm, which determines how to modify the filter coefficients to minimize the cost on the next iteration. The cost function is a criterion used to achieve the desired performance of the filter, where the desired performance may be, for example, minimizing the noise component of the filter input.

Figure 2:
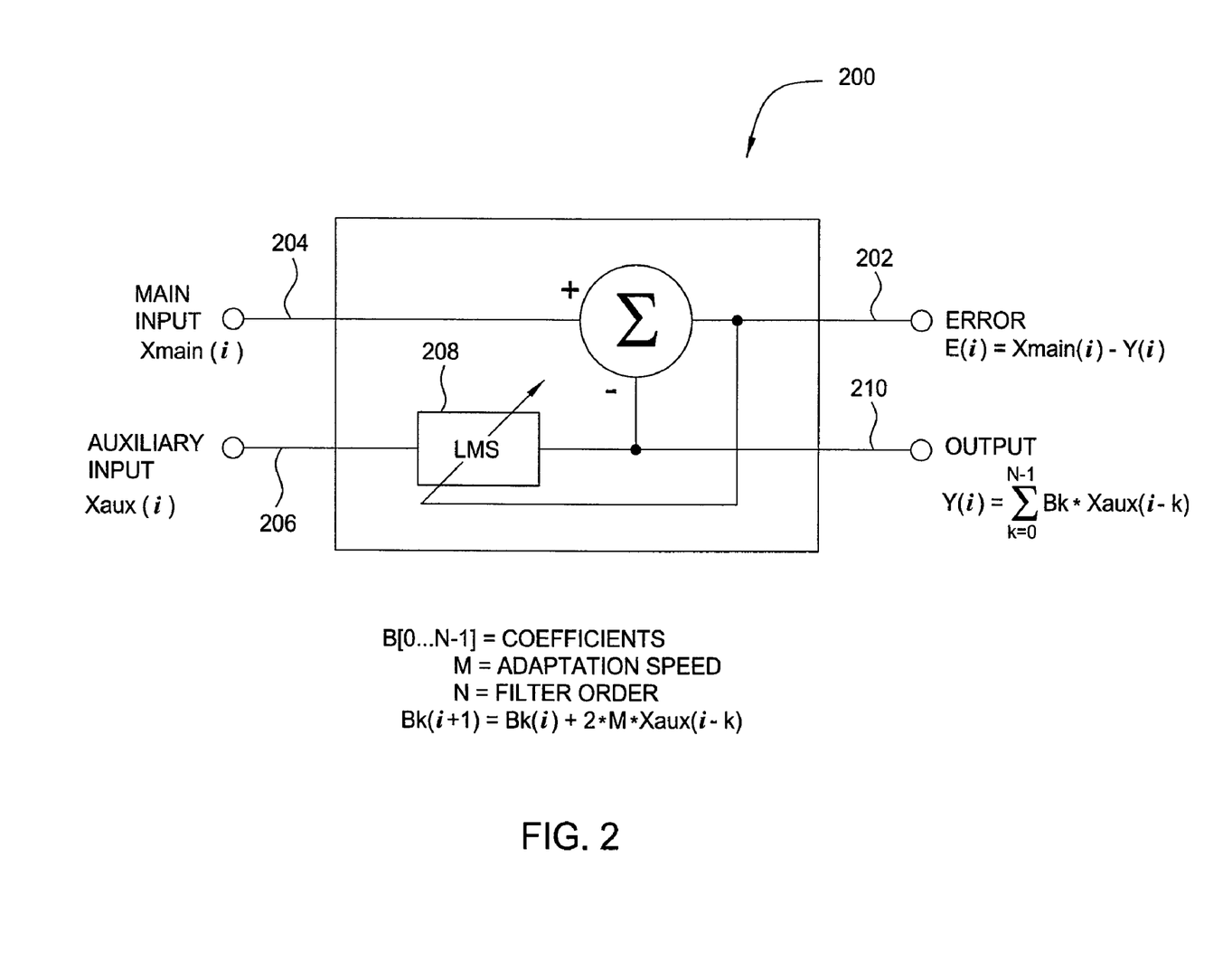
FIG. 2 is a schematic symbol of one embodiment of an exemplary least mean squares (LMS) adaptive filter.

FIG. 2 is a schematic symbol of one type of adaptive filter, which uses a least mean squares (LMS) algorithm, otherwise known as the Widrow-Hoff learning algorithm. In the LMS adaptive filter 200, the LMS algorithm may be used in an effort to find the filter coefficients that relate to producing the least mean squares of the error signal 202, or E(i), or the difference between the desired signal (e.g., the signal received on the main input 204, or Xmain(i)) and the filtered actual signal (e.g., the filtered signal received on the auxiliary input 206, or Xaux(i), with the filtered signal being $$Y(i) = \sum_{k=0}^{N-1} Bk * Xaux(i-k))$$

such that E(i)=Xmain(i)−Y(i). The LMS adaptive filter 200 may use the method of steepest descent to find a coefficient vector (B[0 . . . N−1], where N is the filter order) which minimizes the cost function, where the variable filter 208 may be implemented in a finite impulse response (FIR) form (e.g., Bk(i+1)=Bk(i)+2*M*Xaux(i−k), where M is adaptation speed). For some LMS adaptive filters, the estimated signal 210 (i.e., the output of the variable filter 208, or Y(i)) may also be a signal of interest as shown in FIG. 2.

An Exemplary Full Spectrum Adaptive Filter

Figure 3:
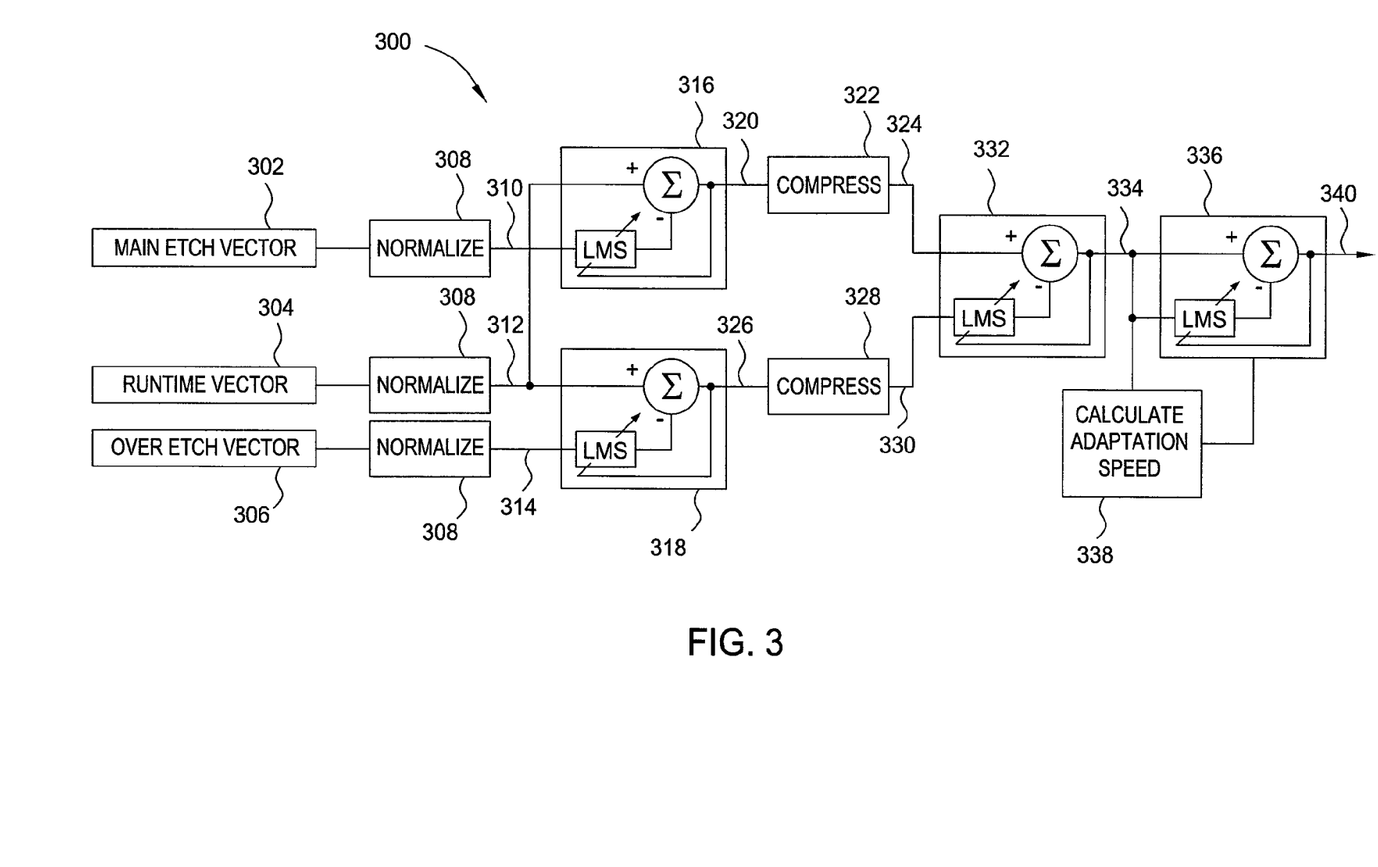
FIG. 3 is a block diagram of one embodiment of exemplary full spectrum adaptive filtering (FSAF) using the LMS adaptive filter of FIG. 2.

Now that LMS adaptive filters have been explained, FIG. 3 is a block diagram of a full spectrum adaptive filter 300 employing such filters according to embodiments of the invention. The adaptive filter 300 may have three inputs: a main etch vector 302, a runtime vector 304, and an over etch vector 306. These inputs may be spectral vectors (or spectral arrays potentially converted into vectors) representing the optical emission spectrum (OES) from the plasma 104 as detected by the optical detector 120 during different phases of the etching process. Since full spectrum adaptive filtering according to embodiments of the invention need not detect and focus on a particular wavelength, the input vectors may contain OES data in any order, and different wavelength may overlap each other. However, the structure of the vectors, such as the order of the wavelengths, should match between the three inputs.

The over etch vector 306 may represent a typical OES of the plasma 104 once over etching has occurred, while the main etch vector 302 may represent a typical OES of the plasma 104 after etching has started, but before the etch endpoint has occurred of the same or a similar substrate run of interest. The runtime vector 304 may represent the OES of the plasma 104 in the current etch process as it is occurring. While the over etch and main etch vectors 306, 302 remain static during the endpoint detection techniques described herein, the runtime vector 304 should be a function of process time. The main etch, runtime, and over etch vectors 302, 304, 306 may be representative of optical emission spectrums encompassing the full optical bandwidth or, for some embodiments, the spectrums may be bandlimited to a desired bandwidth.

For some embodiments, other reference OES vectors besides a main etch vector and an over etch vector may be utilized. For example, in cases where it may be desirable to know when a desired amount of material, in some cases less than all of the overlying material, has been removed, a reference vector representing a typical OES of the plasma 104 in this state and before over etching may be used in place of the over etch vector 306. For clarity of explanation, however, the remainder of the description will only consider the main etch and over etch vectors as the reference vectors.

For some embodiments, the resolution of the OESs may be the same for all three vectors 302, 304, 306 such that they have the same vector size. A typical OES resolution may be around 0.5 nm. However, if any one of the vectors represents a spectrum with a different resolution, the size of the vectors may be equated using any suitable mathematical technique known to those skilled in the art, such as interpolation or least squares approximation, in an effort to furnish "missing" elements to the smaller vector(s).

Furthermore for some embodiments, the vectors 302, 304, 306 may be normalized according to Equation 1 below in a normalization routine 308:

$$\text{for } (i = 0 \rightarrow \text{size} - 1) : \text{out}(i) = \frac{\log(in(i))}{\sum_{k=0}^{size-1} in(k)} \quad (1)$$

where size is the size of the input vector, in(i) is the input spectrum vector at i, and out(i) is the normalized output spectrum vector at i. Normalization may prevent comparator overflow by ensuring that vectors with different magnitudes may still be processed in the full spectrum adaptive filter 300. Although other normalization options besides Equation 1 are available and known to those skilled in the art, normalization according to Equation 1 may also boost the desired signal content with the use of the logarithm function as an added benefit.

As illustrated in FIG. 3, the normalized main etch vector 310 and the normalized runtime vector 312 may be input to the auxiliary input 206 and the main input 204, respectively, of a first LMS adaptive filter 316. The normalized over etch vector 314 and the normalized runtime vector 312 may be input to the auxiliary input 206 and the main input 204, respectively, of a second LMS adaptive filter 318. The first and second LMS adaptive filters 316, 318 may have matching filter orders and adaptation speeds.

With normalized spectrum vectors as inputs to both filters, the first and second LMS adaptive filters 316, 318 may operate in the "spectrum" domain to compare the vectors and may have significant filter order without introducing unacceptable comparator delay in the time domain. The filter order may be large enough to maintain resolved spectrum lines, which are dictated by the resolution of the input spectrums, but small enough to minimize computation cost. For example, a typical CCD-based optical sensor may collect spectrum data ranging from 200-800 nm with a resolution of 0.5 nm every 100 ms, thereby requiring a sampling speed of at least 12 kS/s. A typical filter order for the first and second LMS adaptive filters 316, 318 may be around 10.

The error output 320 of the first LMS adaptive filter 316 may be compressed according to a compression routine 322 in an effort to form an error value 324 associated with a comparison of the normalized runtime vector 312 and the normalized main etch vector 310. In a similar manner, the error output 326 of the second LMS adaptive filter 318 may be compressed according to a compression routine 328 in an effort to form an error value 330 associated with a comparison of the normalized runtime vector 312 and the normalized over etch vector 314. To generate the error values 324, 330, the compression routines 322, 328 may accumulate the absolute values of the error outputs 320, 326 according to Equation 2 below:

$$\text{for } (i = 0 \to \text{size} - 1) : \text{out} = \sum_{i=0}^{\text{size}-1} |in(i)| \quad (2)$$

where size is the size of one of the error output spectrum vectors 320, 326, in(i) is the error output spectrum vector at i, and out is one of the error values 324, 330, a scalar value instead of a vector. By summing the absolute values of the error output spectrum vectors 320, 326, compression according to Equation 2 may boost the desired signal information by enhancing the differences (whether positive or negative) between the compared vectors. Other compression algorithms (e.g., summing the elements of the error output spectrum vector) known to those skilled in the art may be employed.

The scalar error values 324, 330 may be input to the main and auxiliary inputs of a third LMS adaptive filter 332 for comparison. To eliminate comparator output delay, the third LMS adaptive filter 332 may have a minimum filter order of 1. The error output 334 of the third LMS adaptive filter may be input to both the main and auxiliary inputs of a fourth LMS adaptive filter 336. The filter order of the fourth LMS adaptive filter 336 should be equal to 1. While the adaptation speed of the first 316, second 318, and third LMS adaptive filters 332 may be static, the adaptation speed of the fourth LMS adaptive filter 336 may be calculated-dynamically in an adaptation speed routine 338 and variable through several iterations according to Equation 3 below:

$$M = \frac{1}{\text{Max}|in(i)| * \text{Max}|in(i)|} \quad (3)$$

where M is the adaptation speed of the fourth LMS adaptive filter 336 and in(i) is the error output 334 of the third LMS adaptive filter 332 input to the fourth LMS adaptive filter 336 at iteration i. Due to the "aggressive" nature of the fourth LMS adaptive filter's dynamic adaptive speed, the error output 340 of the fourth LMS adaptive filter 336 may exhibit a sharp transition when reference vectors are reached, thereby offering a suitable comparator output trace for etch endpoint detection, as described in further detail below.

Although not shown in FIG. 3, multiple LMS adaptive filters similar to the fourth LMS adaptive filter 336 may be cascaded in an effort to boost comparator output if desired. The main and auxiliary inputs to each of these cascaded LMS adaptive filters may be the output from the previous filter, and the output of the final cascaded LMS adaptive filter may be used as the comparator output trace for etch endpoint detection.

By using spectrum vectors rather than time domain data, full spectrum adaptive filtering as described herein need not require a large amount of data or lots of computational power and thus, may be suitable for embedded applications. Furthermore, because the amount of computation is small when compared to conventional endpoint detection techniques, endpoint detection may occur with very little, if any, delay so that etching may be stopped immediately after endpoint detection if so desired. As an additional advantage, no substrate-to-substrate algorithm configuration adjustments are required since FSAF may provide automatic fine-tuning with the comparisons performed by the first three LMS adaptive filters against the reference vectors.

An Exemplary Method of Endpoint Detection

Figure 4:
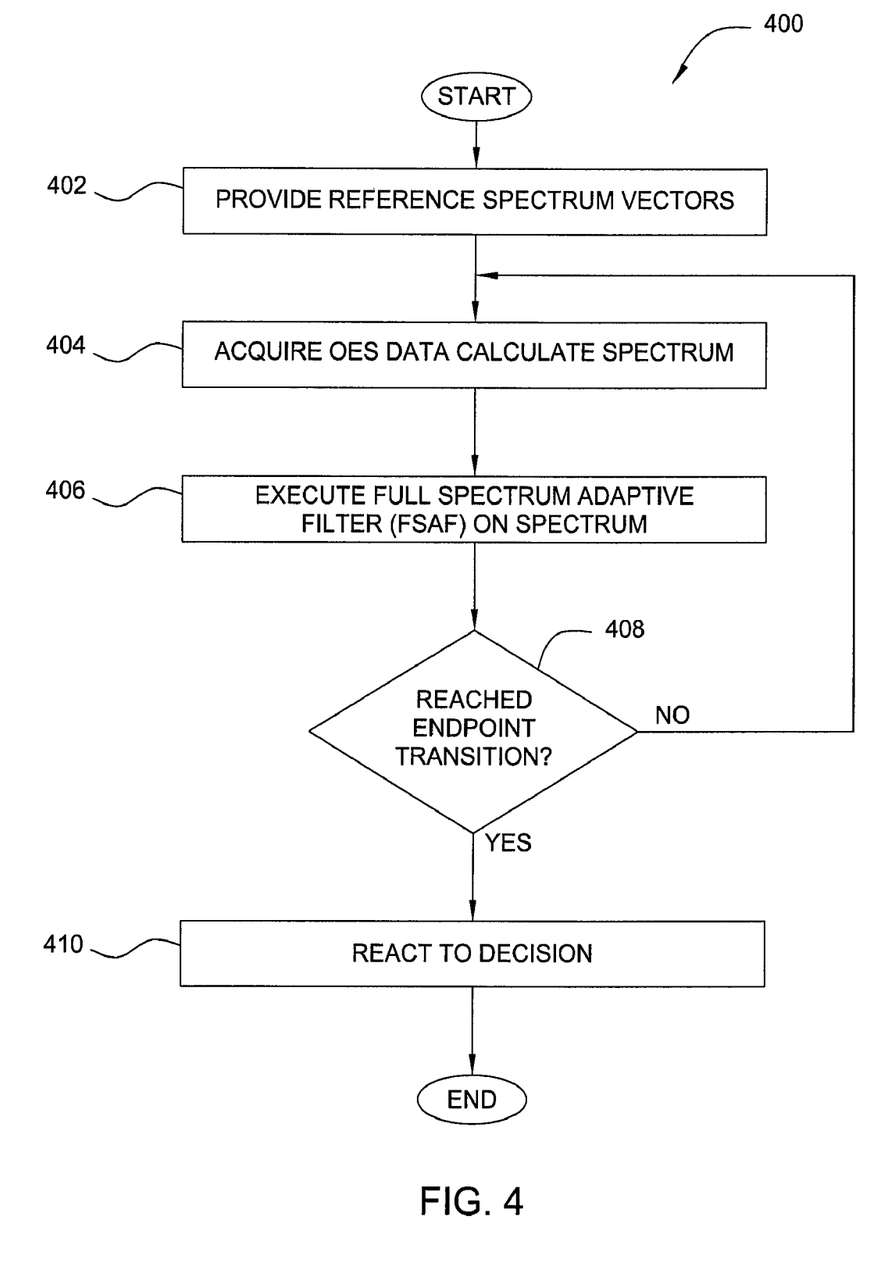
FIG. 4 is a flow diagram of one embodiment of exemplary use of FSAF for endpoint detection during substrate etching.

Referring now to FIG. 4, a flow diagram 400 of using full spectrum adaptive filtering (FSAF) for endpoint detection during substrate etching is depicted. In box 402, the reference optical emission spectrum (OES) vectors, such as the main etch vector 302 and the over etch vector 306, may be provided. These reference vectors may have been generated previously from the current substrate processing run or another substrate processing run similar to the current run.

For low open area substrate processing, reference OES vectors from similar substrate processing with larger open area may be collected and provided. Reference vectors from substrates with larger open area may have better signal-to-noise ratio (SNR) than those with low open area, which may be critical for reliable endpoint detection. As an alternative if large open area data is not available, several reference vectors from low open area substrate processing runs may be averaged to obtain averaged reference vectors, most likely with increased SNR when compared to a single reference vector.

In box 404, runtime OES data may be acquired by detecting optical emissions from the plasma 104 with, for example, the optical detector 120 or the optical sensing portion of a spectrometer or interferometer and calculating the corresponding spectrum. This runtime OES spectrum may encompass the full optical bandwidth (or wavelengths) or may be bandlimited to a bandwidth of interest.

In any case, a spectrum adaptive filter (e.g., the full spectrum adaptive filter 300 of FIG. 3) may be executed on the reference vectors and the runtime OES vector in box 406 as described above. The FSAF may be performed by the signal analyzer 122, whether the signal analyzer is part of a computer or embedded application. The error output 340 of the fourth LMS adaptive filter 336 may be output, stored, and/or plotted (e.g., FSAF plots in FIGS. 5-8 described below) in an effort to determine when an etch endpoint transition has occurred. An endpoint transition may be determined by any suitable means, such as graphically, by crossing a threshold level, or taking the derivative of the output trace to scan for transitions.

If an endpoint transition has not yet occurred, substrate processing may continue in the reaction chamber 102, another runtime OES may be acquired in box 404, and the new runtime OES may be compared in another execution of the full spectrum adaptive filter 300 in box 406 until an endpoint transition has occurred or the loop times out, for example. Once an endpoint transition has been reached, the substrate etching system may automatically react to the decision in box 410 by stopping the etch process immediately or delaying for a predetermined amount of time before stopping the etch process in an effort to ensure complete etching of the substrate 138 in the desired areas. An operator may also manually react to the detection of an endpoint transition in box 408 and stop etching of the substrate 138 immediately or after a predetermined amount of time in box 410.

Figure 5:
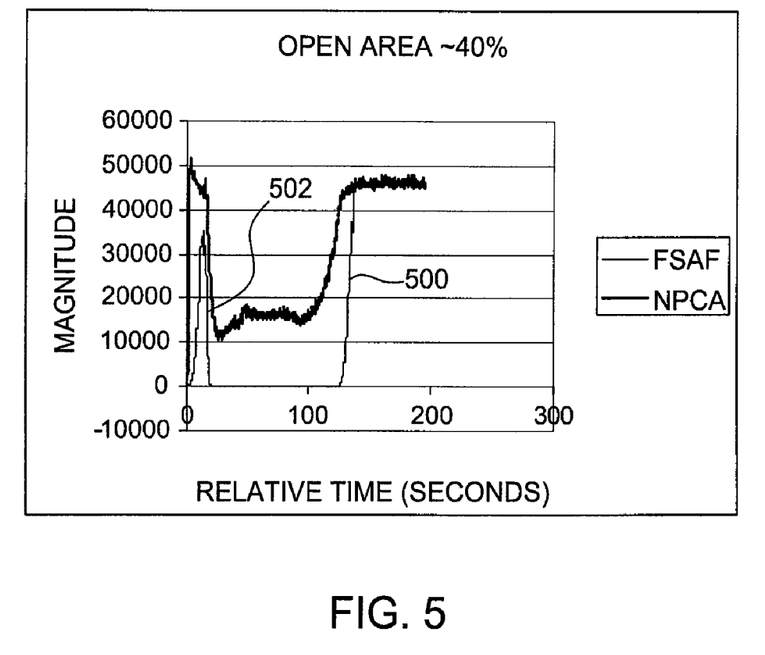
FIGS. 5-8 are exemplary plots of magnitude versus relative time in seconds for FSAF and neural principle component analysis (NPCA) for different open areas.
Figure 6:
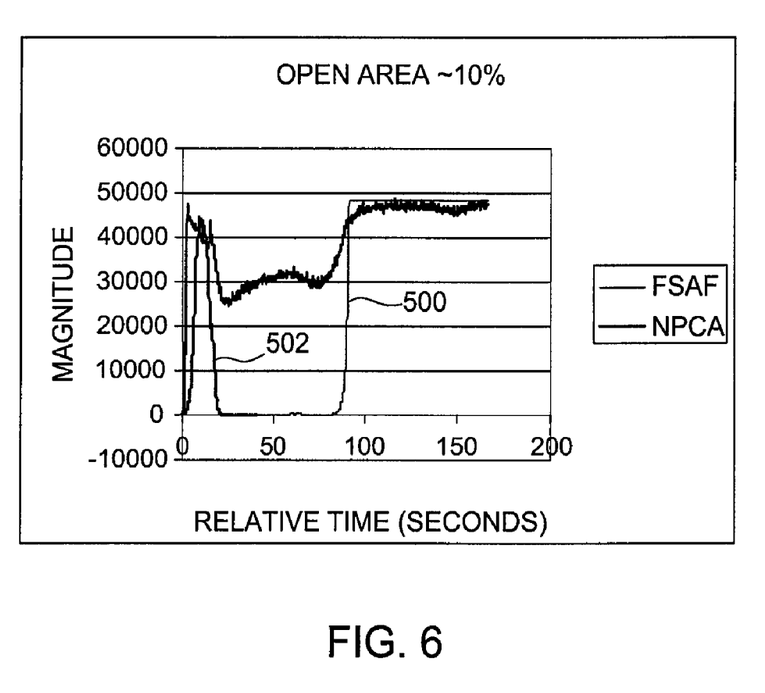
Figure 7:
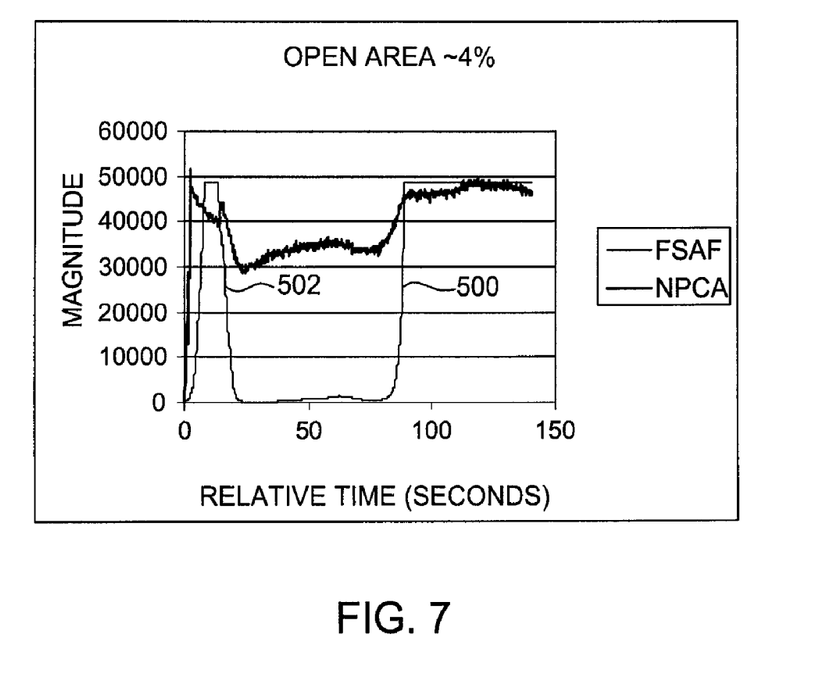
Figure 8:
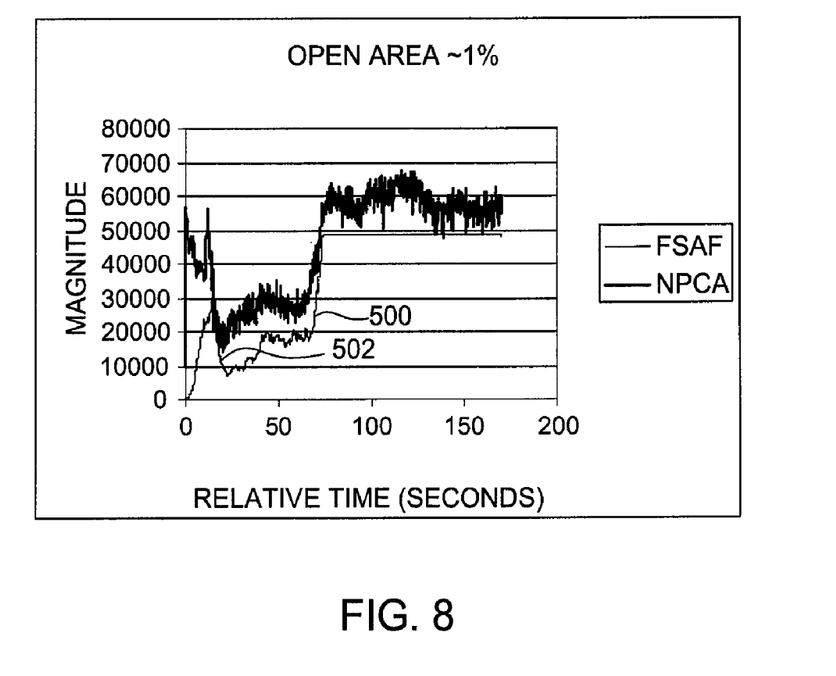

FIGS. 5-8 illustrate plots of the error output 340 of the full spectrum adaptive filter 300 for full spectrum adaptive filtering versus relative time in seconds during substrate etching, where the substrate was poly silicon sandwiched between nitride layers. FIG. 5 depicts endpoint detection using FSAF for a substrate with an open area of approximately 40%. The second rising transition 500 may indicate etch endpoint, and etching of the substrate 138 may be stopped immediately on the rising edge or shortly thereafter. The first falling transition 502 may indicate that the etching of the current substrate has reached the processing point in time where the main etch OES vector 302 was generated such the optical emissions from the plasma 104 are similar. FIGS. 6, 7, and 8 portray endpoint detection using FSAF for a substrate with open areas of approximately 10%, 4%, and 1%, respectively. In generating FIGS. 5-8, the two reference OES vectors were collected at 30 and 150 seconds during 40% open area substrate processing and provided for all of the FSAF endpoint detections shown at 40%, 10%, 4%, and 1% open area.

For comparison purposes, a plot of endpoint detection using neural principle component analysis (NPCA) is also graphed in FIGS. 5-8. Generally speaking, FSAF illustrates that a more definitive, marked endpoint may be detected and a better signal to noise ratio may be achieved when compared to NPCA techniques, even for open areas as low as 1%. Thus, not only is FSAF a significantly faster filter than conventional NPCA techniques, but FSAF is generally more precise at etch endpoint detection, too.

While the foregoing is directed to embodiments of the present invention, other and further embodiments of the invention may be devised without departing from the basic scope thereof, and the scope thereof is determined by the claims that follow.

The invention claimed is:

1. A method of detecting a desired etch state while etching a substrate, the method comprising:
   (a) providing first and second reference spectrums;
   (b) detecting optical emissions during etching of the substrate to generate a runtime optical emission spectrum (OES);
   (c) comparing the runtime OES with the first and second reference spectrums using adaptive filtering to generate a comparator output; and
   (d) repeating (b) and (c) until the desired etch state is detected based on the comparator output.

2. The method of claim 1, wherein the desired etch state is an etch endpoint just before over etching.

3. The method of claim 2, further comprising stopping the etching of the substrate immediately or after a predetermined amount of time has passed after the etch endpoint is detected.

4. The method of claim 1, wherein the first reference spectrum is a main etch OES vector and the second reference spectrum is an over etch OES vector.

5. The method of claim 1, wherein comparing the runtime OES with the first and second reference spectrums comprises:
   comparing the runtime OES with the first reference spectrum in a first adaptive filter having a first error output;
   comparing the runtime OES with the second reference spectrum in a second adaptive filter having a second error output;
   compressing the first error output to for a first compressed error value;
   compressing the second error output to form a second compressed error value;
   comparing the first and second compressed error values in a third adaptive filter having a third error output; and
   buffering the third error output with a fourth adaptive filter having a fourth error output used for the comparison.

6. The method of claim 1, wherein detecting the optical emissions comprises using a charge-coupled device (CCD)-based optical sensor or a Fabray-Perot interferometer.

7. A computer-readable medium containing a program for detecting a desired etch state while etching a substrate, which, when executed by a processor, performs operations comprising:
   (a) providing first and second reference spectrums;
   (b) detecting optical emissions during etching of the substrate to generate a runtime optical emission spectrum (OES);
   (c) comparing the runtime OES with the first and second reference spectrums using adaptive filtering to generate a comparator output; and
   (d) repeating (b) and (c) until the desired etch state is detected based on the comparator output.

8. The computer-readable medium of claim 7, wherein the desired etch state is an etch endpoint just before over etching.

9. The computer-readable medium of claim 7, wherein the first reference spectrum is a main etch OES vector and the second reference spectrum is an over etch OES vector.

* * * * *